(12) United States Patent
Kubo

(10) Patent No.: US 9,707,359 B2
(45) Date of Patent: Jul. 18, 2017

(54) POWDER SPRAYING DEVICE

(75) Inventor: Tomohiko Kubo, Osaka (JP)

(73) Assignee: NIPRO CORPORATION, Osaka (JP)

( * ) Notice: Subject to any disclaimer, the term of this patent is extended or adjusted under 35 U.S.C. 154(b) by 1104 days.

(21) Appl. No.: 13/882,312

(22) PCT Filed: Jan. 12, 2012

(86) PCT No.: PCT/JP2012/050528
§ 371 (c)(1),
(2), (4) Date: Apr. 29, 2013

(87) PCT Pub. No.: WO2012/096356
PCT Pub. Date: Jul. 19, 2012

(65) Prior Publication Data
US 2013/0218072 A1   Aug. 22, 2013

(30) Foreign Application Priority Data
Jan. 14, 2011   (JP) .................. 2011-006074

(51) Int. Cl.
*A61M 13/00* (2006.01)
*A61M 11/06* (2006.01)
*A61M 15/00* (2006.01)

(52) U.S. Cl.
CPC ............ *A61M 13/00* (2013.01); *A61M 11/06* (2013.01); *A61M 15/0006* (2014.02);
(Continued)

(58) Field of Classification Search
CPC .............. A61M 11/06; A61M 15/0006; A61M 15/0008; A61M 2202/064; A61M 2205/8218
See application file for complete search history.

(56) References Cited

U.S. PATENT DOCUMENTS

| 5,033,463 A | 7/1991 | Cocozza |
| 5,372,128 A | 12/1994 | Haber et al. |
| 5,445,612 A | 8/1995 | Terakura et al. |

FOREIGN PATENT DOCUMENTS

| JP | A-3-184563 | 8/1991 |
| JP | B2-2809976 | 10/1998 |

(Continued)

OTHER PUBLICATIONS

Jul. 16, 2013 International Preliminary Report on Patentability issued in International Patent Application No. PCT/JP2012/050528.

(Continued)

*Primary Examiner* — Rebecca E Eisenberg
(74) *Attorney, Agent, or Firm* — Oliff PLC

(57) ABSTRACT

The invention is configured so that pressurized gas from a pressurized gas supply source passes through a pressurized gas channel provided in a main body of a powder spraying device and is sprayed out. A powder container containing powder such as medical agents is provided on the main body. The powder within the powder container is supplied to the pressurized gas channel and is sprayed together with the pressurized gas. An eccentric rotor with a center of gravity deviated from a center of rotation is provided in the main body. When spraying the powder together with the pressurized gas, vibrations are applied to the main body and the powder container by a rotation of the eccentric rotor. The powder can be thereby mixed more evenly with the pressurized gas.

5 Claims, 4 Drawing Sheets

(52) U.S. Cl.
CPC ... *A61M 15/0008* (2014.02); *A61M 2202/064* (2013.01); *A61M 2205/8218* (2013.01)

(56) References Cited

FOREIGN PATENT DOCUMENTS

| | | |
|---|---|---|
| JP | A-10-305258 | 11/1998 |
| WO | WO 2006/075184 A1 | 7/2006 |
| WO | WO 2010/070333 A2 | 6/2010 |

OTHER PUBLICATIONS

Feb. 28, 2012 International Search Report issued in International Patent Application No. PCT/JP2012/050528.
Extended European Search Report issued in European Patent Application No. 12734269.9 on Jul. 16, 2014.

POWDER SPRAYING DEVICE

TECHNICAL FIELD

The present invention relates to a powder spraying device, more specifically a powder spraying device favorably used to spray hemostatic agents and the like in powder form onto the lesion in the patient's body.

BACKGROUND ART

Conventionally, as this type of powder spraying device, there has been known a device comprising a main body of the powder spraying device, a powder container attached to the main body that contains powder such as medical agents, a pressurized gas channel provided on said main body where the powder in said powder container is supplied, and a pressurized gas supply source that supplies pressurized gas to said pressurized gas channel, wherein the powder within the above powder container is supplied to the pressurized gas supplied from said pressurized gas supply source to said pressurized gas channel in order to spray said powder together with the pressurized gas (Patent Document 1).

In using this powder spraying device to supply the powder within the powder container to the pressurized gas, once said pressurized gas is sprayed into the powder container, the powder is stirred within the powder container by the spraying so as to be mixed with the pressurized gas, and then said powder is discharged out of the powder container together with the pressurized gas to be further sprayed onto the lesion in the patient's body and the like.

BACKGROUND ART DOCUMENTS

Patent Documents

Patent Document 1: JP PAT No. 2809976

SUMMARY OF THE INVENTION

Problem The Invention Attempts To Solve

In a conventional powder spray device, powder is properly mixed with pressurized gas by the spraying of the pressurized gas into a powder container, but since the amount of powder mixed with gas is reduced as the amount of powder within the powder container decreases, there is a risk of failing to efficiently supply enough amount of powder to a nozzle all the way to the completion.

The present invention is made in view of such a situation to provide a powder spraying device whereby enough amount of powder is supplied to the nozzle for spraying at any moment during use.

Means For Solving The Problem

The present invention provides a powder spraying device including a main body thereof, a powder container attached to the main body that contains powder such as medical agents, a pressurized gas channel provided in the main body to which the powder within the powder container is supplied, and a pressurized gas supply source that supplies pressurized gas P to the pressurized gas channel, the powder within the powder container being supplied to the pressurized gas P supplied to the pressurized gas channel from the pressurized gas supply source to be sprayed out together with the pressurized gas P, the device being characterized by that an eccentric rotor with a center of gravity deviated from a center of rotation is provided in the main body in a rotatable manner, and a rotation drive means is provided that rotates the eccentric rotor to apply vibrations to the main body and the powder container by a rotation of the eccentric rotor when the powder is sprayed out together with the pressurized gas P.

EFFECT OF THE INVENTION

According to the present invention, when the powder is sprayed together with the pressurized gas, vibrations can be applied to the above main body and the powder container by the rotation of the eccentric rotor so that the powder substantially fluidized by the powder fluidization within the powder container caused by the vibrations can be supplied from the powder container into the channel, which allows the powder to be mixed more evenly with the pressurized gas P in a situation where only a small amount of powder is left as compared to the conventional devices with no vibration.

EMBODIMENTS FOR CARRYING OUT THE INVENTION

Figure 1:
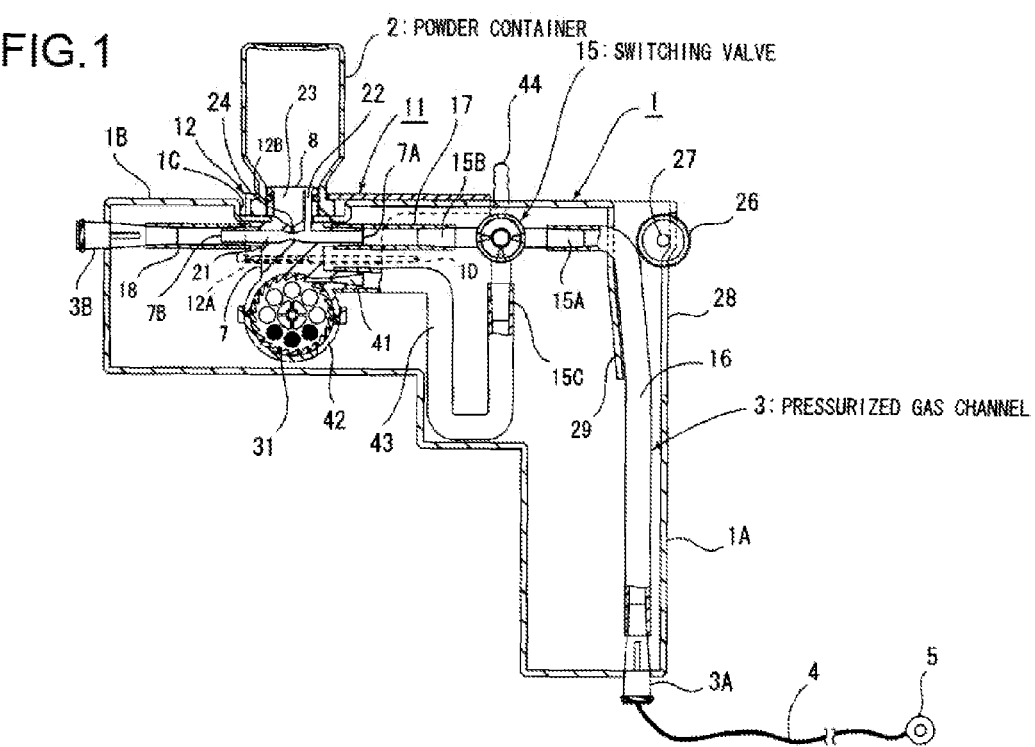
FIG. 1 is a cross-section showing a first embodiment of the present invention.

The present invention is described below in reference to the embodiments shown in the drawings. In FIG. 1, a main body 1 of the powder spraying device is configured approximately in a form of an L-shaped pistol, and the portion extending down therefrom is a grip portion 1A, which can be gripped for use.

Meanwhile, the portion extending in a horizontal direction of the above L-shaped main body 1 is a barrel portion 1B, on top of which a powder container 2 containing powder such as hemostatic agents can be detachably attached upside down.

Figure 2:
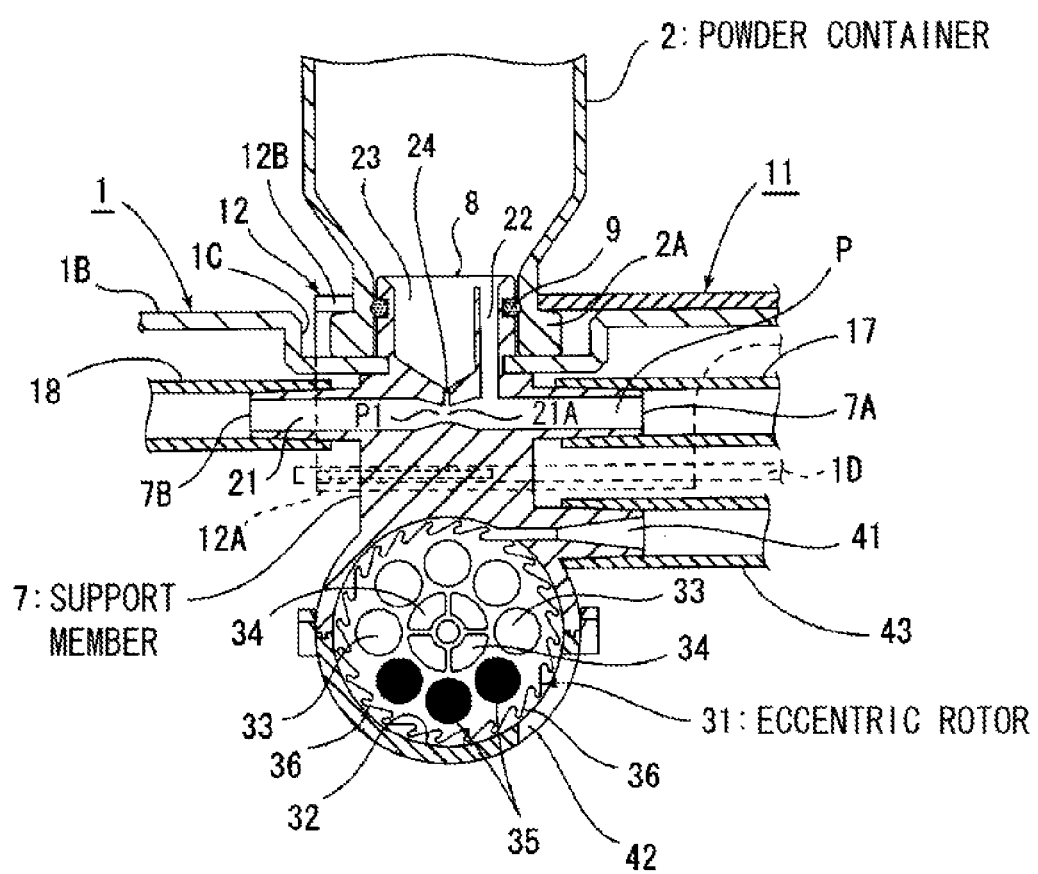
FIG. 2 is an enlarged cross-section of FIG. 1.

Within the above main body 1, a pressurized gas channel 3 is provided all the way between a connector 3A provided at the bottom of the grip portion 1A and a connector 3B provided at the tip end of the barrel portion 1B so that the powder within the above powder container 2 can be supplied to pressurized gas P that flows through the pressurized gas channel 3 (see FIG. 2).

To the connector 3A on the side of the above grip portion 1A, one end of a flexible hose 4 can be detachably connected, and the other end of said flexible hose 4 is connected to as pressurized gas supply source 5.

Also, to the connector 3B on the side of the barrel portion 1B, a nozzle, not shown, that can be used favorably to spray powder such as the above hemostatic agents and the like onto the patient's lesion can be connected, it is also possible to spray powder directly to the lesion from this connector 3B as necessary.

The above main body 1 is attached with a support member 7 for detachably attaching the above powder container 2 on said main body As shown in the enlarged cross-section in FIG. 2, the support member 7 is provided with a cylinder portion 8 on the upper end thereof extending in a cylindrical shape and is fixed to the main body 1 in such a way that the upper end of the cylinder portion 8 protrudes upward from the main body 1. The support member 7 and the cylinder portion 8 are part of a vibration unit for vibrating the powder container.

A concave portion 1C in a cylindrical shape is formed on the upper surface of the above main body 1, and the above cylinder portion 8 is provided in concentric with the interior of the concave portion 1C. Along the outer periphery of the cylinder portion 8 at the tip end of the protrusion above the main body 1, a sealing member 9 in an annular shape is provided.

The opening of the above powder container 2 is provided with an inner peripheral surface in a cylindrical shape so that, when the cylinder portion 8 of the above support member 7 is fitted into said inner peripheral surface, both of these can be connected in a detachable manner with airtightness maintained due to the elasticity of the above sealing member 9. As one of the methods of connecting the powder container in lieu of the cylinder portion 8, a hollow puncture needle type joint that is formed to be puncture connected to the powder container can be used.

Also, an anti-falling means 11 is provided to prevent the powder container 2 from falling off the main body 1, which will be described later in detail.

As shown in FIG. 1, the above pressurized gas channel 3 is provided with a tube 16 that connects the connector 3A on the side of the above grip portion 1A and an inlet port 15A of a switching valve 15 provided for switching the flow within the pressurized gas channel 3.

Also, the above pressurized gas channel 3 is provided with a tube 17 that connects a first outlet port 15B of the above switching valve 15 and an inlet port 7A provided in the above support member 7, as well as a tube 18 that connects an outlet port 7B provided in the support member 7 and the connector 3B on the side of the above barrel portion 1B.

Then, as shown in FIG. 2, the inlet port 7A and the outlet port 7B provided in the support member 7 are communicated by a channel 21, and a constricted portion 21A is formed to produce a Venturi effect at the center of said channel. An introduction channel 22 is formed to fork out the channel 21 on the upstream side of said constricted portion 21A, which penetrates through the above cylinder portion 8 to communicate with the inside of the powder container 2 so as to supply the pressurized gas P into said powder container 2.

Also, in order to smoothly introduce powder within the powder container 2 to the above constricted portion 21A, a guiding channel 23 is formed in the above cylinder portion 8 in a reverse circular cone shape tapering towards the bottom, and the bottom end of this guiding channel 23 and the center of the above constricted portion 21A are communicated by a communication channel 24 with a small diameter.

Therefore, the pressurized gas P introduced to the inlet port 7A is also introduced into the powder container 2 via the introduction channel 22. At this time, since vibrations are applied by a vibration unit to the powder container 2, the powder within the container exists in the guiding channel 23 in a state of fluidization and blocks the communication channel 24 all the time.

Meanwhile, the pressurized gas P introduced to the above inlet port 7A passes through the channel 21 and the constricted portion 21A at the center thereof to be discharged out from the outlet port 7B, and in so doing, the constricted portion 21A causes a Venturi effect to generate pressurized gas P1 at a lower pressure than the pressurized gas P (see FIG. 2). This causes the powder collected in the guiding channel 23 in a state of fluidization to be sucked in by the pressurized gas P1 that passes through the constricted portion 21A via the communication channel 24 and then supplied to the channel 21 to be sprayed out from the connector 3B after flowing through the tube 18.

Furthermore, as shown FIG. 1, a clamp roller 26 is provided at the upper end of the above grip portion 1A. The clamp roller 26 is provided with a shaft member 27 at its center protruding out on both sides, and part of the outer periphery of the clamp roller 26 sticks out from a slit 28 formed in the up-and-down direction at the upper end of the grip portion 1A, while each end of the shaft member 27 is made to abut against the inner walls of the grip portion 1A in a rollable pliable manner.

Meanwhile, the tube 16 is arranged along a holding plate 29 provided in the up-and-down direction within the above grip portion 1A, and the holding plate 29 and the inner walls of the grip portion 1A are set to gradually get closer to each other as they move downward.

Therefore, the tube 16 can be crushed gradually between the outer periphery of the clamp roller 26 and the holding plate 29 by gradually rolling the clamp roller 26 downward keeping the tube 16 sandwiched between the outer periphery of the clamp roller 26 and the holding plate 29, which makes it possible, by the amount of crushing, to control the flow rate of the pressurized gas P that passes through the tube 16 so that the amount of the pressurized gas P sprayed from the nozzle can be adjusted.

Next, as shown in FIG. 2, at the lower portion of the above support member 7, an eccentric rotor 31 with the center of gravity deviated from the center of rotation that causes vibrations is pivotally supported in a rotatable manner.

The eccentric rotor 31 is formed in a cylindrical shape, and a containing space 32 in a cylindrical shape that contains the eccentric rotor 31 is formed on the above support member 7. The eccentric rotor 31 is pivotally supported by the support member 7 in a rotatable manner in a state of being contained in the containing space 32 in a cylindrical shape so as to keep its rotation axle horizontal, that is, to make the eccentric rotor 31 rotate in a vertical plane.

Eight circular holes 33 are formed along the outer periphery of the above eccentric rotor 31 at equal intervals in the circumferential direction, and in the present embodiment, three adjacent circular holes 33 among the eight circular holes 33 are each provided with a weight 35 to make the weight of the eccentric rotor 31 off balance. As a matter of course, the numbers of the circular holes 33 and the weights 35 can be increased or decreased as necessary.

On the outside of the above eccentric rotor 31, a multitude of fins 36 are formed protruding diagonally toward the rear side in the rotational direction on the basis of counterclockwise rotation of the eccentric rotor 31, and the inner walls in a cylindrical shape that form the above containing space 32 are formed to provide a slight clearance beyond the tip of each fin 36.

The shape and direction and so forth of the rotor are not limited to the above example, but the same effect can be obtained as long as the center of gravity of the rotor is off-centered.

In addition, a spray outlet 41 that sprays the pressurized gas P onto the fins 36 of the eccentric rotor 31 is formed in the above support member 7 in order to rotate said eccentric rotor 31. The spray outlet 41 is formed within the containing space 32 in a cylindrical shape at a position that allows the pressurized gas P to be sprayed at a tangent direction along the inner wails thereof, and the pressurized gas P sent into the containing space 32 in a cylindrical shape is to he discharged out of a discharge outlet 42 formed adjacent to said spray outlet 41 toward the rear side in the rotational direction of the eccentric rotor 31.

As shown in FIG. 1, the above spray outlet 41 and the second outlet port 15C of the above switching valve 15 are connected to each other by a tube 43 that constitutes an additional pressurized gas channel.

The above switching valve 15, when a lever 44 thereof is turned to the horizontal shut-off position, blocks the communication between the inlet port 15A and the outlet ports 15B and 15C to stop the supply of the pressurized gas P to the powder container 2 and the eccentric rotor 31.

Meanwhile, when the lever 44 of the switching valve 15 is turned up vertically to the spraying position, the above inlet port 15A and the outlet ports 15B and 15C are communicated to allow the pressurized gas to be supplied to the powder container 2 and the eccentric rotor 31.

The anti-falling means 11 mentioned above is for preventing the powder container 2 from falling off from the main body 1, but it also serves as a safety means that keeps the lever 44 of the above switching valve 15 from switching between the horizontal closing position and upper vertical spraying position unless the powder container 2 is set securely to the main body 1 to prevent itself from falling off.

In other words, the anti-falling means 11 is provided with a sliding member 12 that can slide along the longitudinal direction of the barrel portion 1B outside thereof. On both sides of the barrel portion 1B along the longitudinal direction, an engaging groove 1D is formed where the sliding member 12 is made to slide along the longitudinal direction of the barrel portion 1B by engaging each of engaging. protrusions 12A provided on both sides of the sliding member 12 with the engaging groove 1D in a slidable manner.

On the upper surface of the above sliding member 12, a slit 12B is formed along the longitudinal direction of the barrel portion 1B on the left side in FIGS. 1 and 2, and when the sliding member 12 is located at the engaging position shown in the Figures, with the powder container 2 attached to the main body 1, the ends on both sides of the slit 12B can be engaged with a flange portion 2A formed along the front outer periphery of e powder container 2 to prevent the powder container 2 from coming off upward.

Under this state, as shown in FIG. 1, the right end of the sliding member 12 is set at a position slightly to the left of the upper vertical position of the lever 44 of the above switching valve 15 to be able to turn up the lever 44 vertically to the spraying position.

Figure 3:
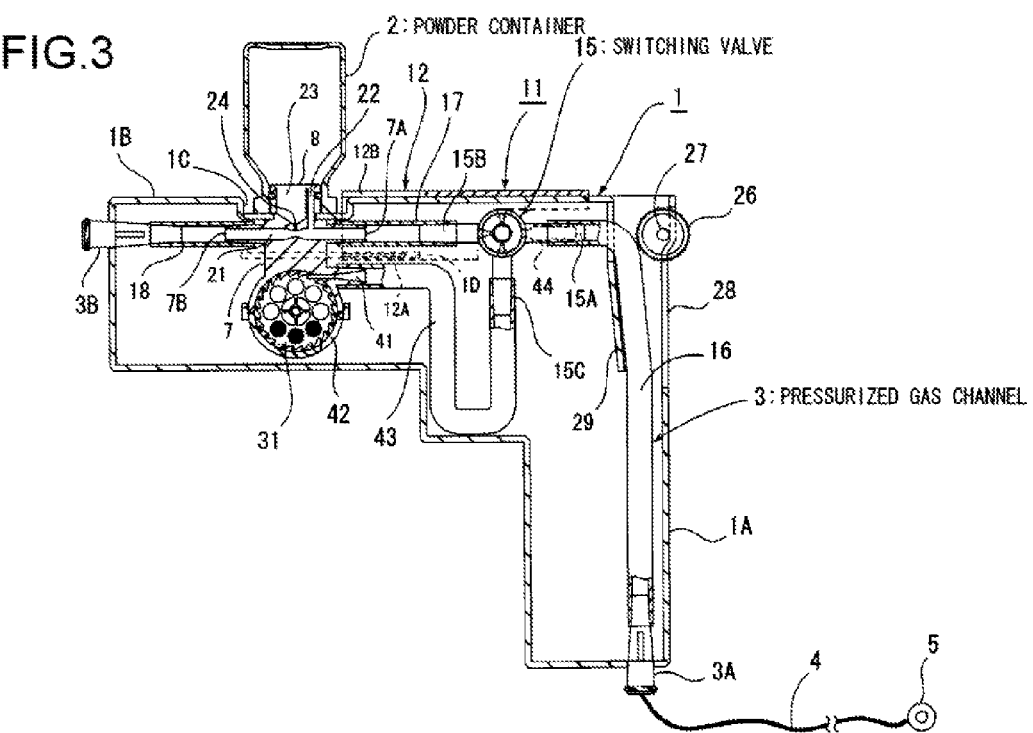
FIG. 3 is a cross-section showing a different state from the one in FIG. 1.

Meanwhile, when the sliding member 12 is moved from the above engaging position to the releasing position to the right, as shown in FIG. 3, engagement between both ends of the slit 12B and the flange portion 2A is released to allow the powder container 2 to be removed upward from the main body 1. At the same time, the right end of the above sliding member 12 now covers the lever 44 of the above switching valve 15 at a horizontal closing position, under which state, the lever 44 cannot be turned up to a vertical spraying position.

According to the configuration described above, before using the powder spraying device, the lever 44 of the switching valve 15 is first turned to a horizontal position so that the pressurized gas P cannot be supplied to the powder container 2 or the eccentric rotor 31. Then, the sliding member 12 of the anti-falling means 11 is moved to the releasing position to the right (conditions of FIG. 3) to allow the powder container 2 to be attached to the main body 1, and at the same time, the above lever 44 at the horizontal closing position is covered by the right end of the sliding member 12 to prevent said lever 44 from being turned up to the vertical spraying position.

Next, one end of the flexible hose 4 is connected to the connector 3A on the side of the grip portion 1A to enable the supply of the pressurized gas P from the pressurized gas supply source 5 to the powder spraying device. At the same time, the powder container 2 containing powder such as hemostatic agents therein is attached to the main body 1.

After the above powder container 2 is attached to the main body 1, the above sliding member 12 is moved to the left to the engagement position (conditions of FIGS. 1 and 2), whereby both ends of the slit 12B are engaged with the flange portion 2A formed along the front outer periphery of the powder container 2 to prevent the powder container 2 from being removed upward from the main body 1. Under this state, the above lever 44 can be turned to the upper vertical spraying position.

Once this state is reached, the lever 44 of the above switching valve 15 is turned to the upper vertical spraying position, with the connector 3B or a nozzle, not shown, being connected thereto and directed toward the patient's lesion. This allows the inlet port 15A and the first outlet port 15B of the switching valve 15 to be communicated so that the pressurized gas P from the pressurized gas supply source 5 can be sprayed out from the above connector 3B via the flexible hose 4, connector 3A, tube 16, inlet port 15A and first outlet port 15B of the switching valve 15, tube 17, inlet port 7A of the support member 7, channel 21, constricted portion 21A, outlet port 7B and tube 18 of the support member 7. At the same time, the powder that has been collected in the guiding channel 23 in a state of fluidization is sucked in by the Venturi effect of the pressurized gas P1 that passes through the constricted portion 21A via the communication channel 24 to be supplied to the channel 21, and passes through the tube 18 to be sprayed out from the connector 3B.

Meanwhile, since the inlet port 15A and second outlet port 15C of the switching valve 15 are also communicated with each other when the lever 44 of the above switching valve 15 is turned up to the vertical position, the pressurized gas P introduced from the pressurized gas supply source 5 to the inlet port 15A gets sprayed into the containing space 32 from the spray outlet 41 via the second outlet port 15C and the tube 43.

This allows the pressurized gas P to be sprayed onto the fins 36 of the eccentric rotor 31 to rotate said eccentric rotor 31 in the counter-clockwise direction, and the pressurized gas P that rotated the eccentric rotor 31 in the counter-clockwise direction is discharged out of the discharge outlet 42.

Once the eccentric rotor 31 is rotated, vibrations start to occur due to the rotation caused by the deviated center of gravity from the center of rotation of said eccentric rotor 31, and the vibrations are applied to the powder container 2 via the support member 7 that pivotally supports said eccentric rotor 31. When the powder container 2 is vibrated, the powder within said powder container 2 is fluidized to stay in the guiding channel 23 in a state of blocking the communication channel 24 all the time, and the powder is securely sucked in toward the channel 21 by the Venturi effect and supplied thereto to be sprayed onto the patient's lesion in a stable manner regardless of the amount of powder within the powder container.

Figure 4:
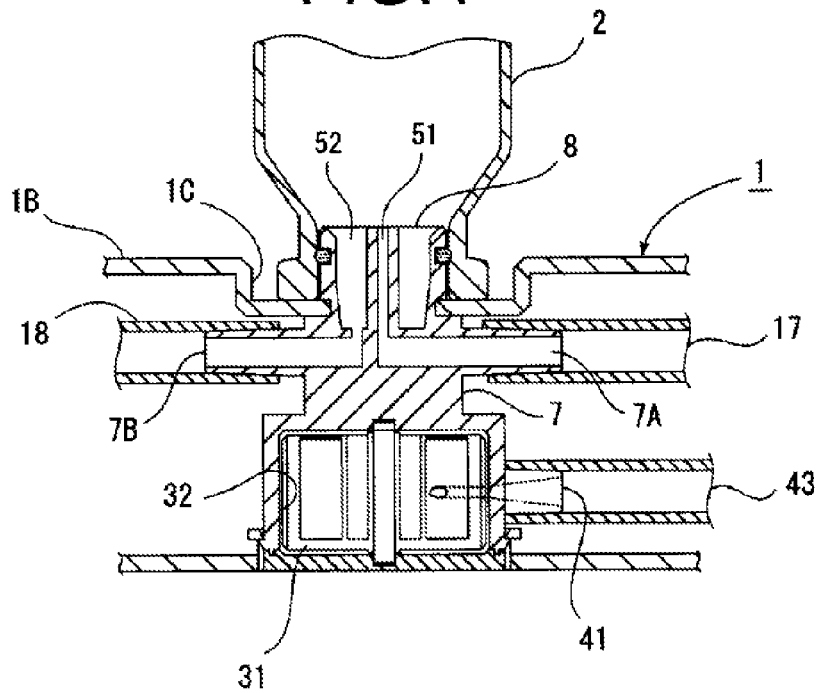
FIG. 4 is an enlarged cross-section showing key portions of a second embodiment of the present invention.

FIG. 4 shows an enlarged cross-section of key portions of a second embodiment of the present invention, and in the present embodiment, unlike the first embodiment, the eccentric rotor 31 is pivotally supported in a rotatable manner by the support member 7 so as to be positioned to make its rotation axle vertical, that is to rotate itself within a horizontal plane. Even in this configuration, it is obvious that vibrations can be applied to the main body 1 and the powder container 2 by the rotation of the eccentric rotor 31.

Also, in the first embodiment, the inlet port 7A and outlet port 7B provided in the support member 7 were directly communicated with each other by the channel 21, but in the present embodiment, the inlet port 7A and outlet port 7B are not directly communicated with each other. In other words, in the present embodiment, an inlet channel 51 communicated with the inlet port 7A is communicated into the powder container 2, and an outlet channel 52 communicated with the outlet port 7B is also communicated into the powder container 2.

Therefore, in the present embodiment, the full amount of the pressurized gas P from the inlet port 7A flows into the powder container 2 via the inlet channel 51, and the pressurized gas P flowed into said powder container 2 so as to stir the powder within thereof flows to the outlet port 7B via the outlet channel 52 in its full amount together with the powder.

Other configurations are made in the same way as those of the first embodiment, and the same or equivalent portions as or to those of the first embodiment are coded by the same numerals as the first embodiment.

Figure 5:
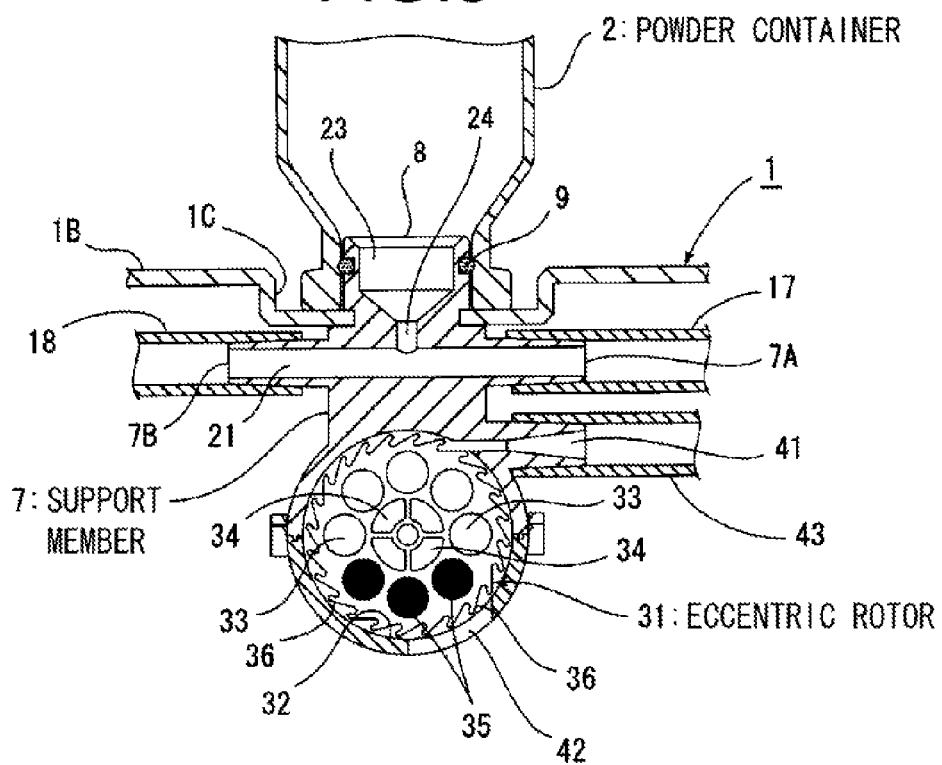
FIG. 5 is an enlarged cross-section showing key portions of a third embodiment of the present invention.

FIG. 5 shows an enlarged cross-section showing key portions of a third embodiment of the present invention. In the present embodiment, as in the above first embodiment, the inlet port 7A and the outlet port 7B provided in the support member 7 are directly communicated with each other by the channel 21, but the constricted portion 21A provided in the channel 21 is omitted. The introduction channel 22 of the first embodiment is also omitted, and the powder within the powder container 2 is made to drop by its own weight into the channel 21 via the guiding channel 23 and communication channel 24.

Other configurations are made in the same way as to those of the first embodiment, and the same or equivalent portions as or to those of the first embodiment are coded by the same numerals as the first embodiment.

Even in this configuration, vibrations can be applied to the main body 1 and the powder container 2 by the rotation of the eccentric rotor 31, whereby the powder within the powder container 2 is favorably dropped into the channel 21 to enable the powder to be mixed more evenly with the pressurized gas P as compared to the conventional devices with no vibration.

In the above embodiments, the rotation drive means that rotates the above eccentric rotor 31 is composed of an additional pressurized gas channel (tube 43, spray outlet 41) that rotates said eccentric rotor 31 by spraying the pressurized gas P onto the fins 36 thereof, but it is not limited to such means but can be a motor drive as a matter of course.

KEYS TO SYMBOLS

1 Main body
1A Grip portion
1B Barrel portion
2 Powder container
3 Pressurized gas Channel
5 Pressurized gas supply source
7 Support member
15 Switching valve
21 Channel
21A Constricted portion
22 Introduction channel
23 Guiding channel
24 Communication channel
31 Eccentric rotor
32 Containing space
41 Spray outlet
42 Discharge outlet

The invention claimed is:
1. A powder spraying device comprising:
a main body thereof;
a powder container attached to the main body that contains powder;
a pressurized gas channel provided in the main body to which the powder within the powder container is supplied;
a pressurized gas supply source that supplies pressurized gas to the pressurized gas channel, the powder within the powder container being supplied to the pressurized gas supplied to the pressurized gas channel from the pressurized gas supply source to be sprayed out together with the pressurized gas;
a support member attached to the main body, wherein
the support member is attached with the powder container,
the support member is further formed with an inlet port and an outlet port that constitute the pressurized gas channel,
the inlet port and the outlet port are communicated with each other by a channel, and
a communication channel communicated into the powder container is formed in the channel to allow the powder within the powder container to be supplied from the communication channel to the channel that communicates between the inlet port and the outlet port;
a constricted portion with a Venturi effect formed in the channel that communicates between the inlet port and the outlet port,
wherein the communication channel is communicated with the constricted portion; and
an eccentric rotor with a center of gravity deviated from a center of rotation is provided in the main body in a rotatable manner, and a rotation drive means is provided that rotates the eccentric rotor to apply vibrations to the main body and the powder container by a rotation of the eccentric rotor when the powder is sprayed out together with the pressurized gas.

2. The powder spraying device according to claim 1, wherein an introduction channel is forked out from the channel on an upstream side of the constricted portion to communicate with an inside of the powder container so as to introduce part of the pressurized gas into the powder container.

3. The powder spraying device according to claim 1, wherein the inlet port and the outlet port are communicated with an inside of the powder container via an inlet channel and an outlet channel, respectively, and the pressurized gas from the inlet port supplied into the powder container via the inlet channel flows to the outlet port via the outlet channel together with the powder.

4. A powder spraying device comprising:

a main body thereof;

a powder container attached to the main body that contains powder;

a pressurized gas channel provided in the main body to which the powder within the powder container is supplied;

a pressurized gas supply source that supplies pressurized gas to the pressurized gas channel, the powder within the powder container being supplied to the pressurized gas supplied to the pressurized gas channel from the pressurized gas supply source to be sprayed out together with the pressurized gas;

an eccentric rotor with a center of gravity deviated from a center of rotation is provided in the main body in a rotatable manner, and a rotation drive means is provided that rotates the eccentric rotor to apply vibrations to the main body and the powder container by a rotation of the eccentric rotor when the powder is sprayed out together with the pressurized gas; and fins formed along an outer periphery of the eccentric rotor, wherein the rotation drive means includes an additional pressurized gas channel that rotates the eccentric rotor by spraying the pressurized gas onto the fins of the eccentric rotor.

5. The powder spraying device according to claim 4, further comprising a switching valve provided on the main body, wherein the pressurized gas channel to which the powder within the powder container is supplied and the additional pressurized gas channel that rotates the eccentric rotor are communicated with the pressurized gas supply source via the switching valve.

* * * * *